US005743855A

United States Patent [19]

Hanafy et al.

[11] Patent Number: 5,743,855

[45] Date of Patent: Apr. 28, 1998

[54] BROADBAND PHASED ARRAY TRANSDUCER DESIGN WITH FREQUENCY CONTROLLED TWO DIMENSION CAPABILITY AND METHODS FOR MANUFACTURE THEREOF

[75] Inventors: Amin M. Hanafy, Los Altos Hills; Samuel H. Maslak, Woodside; Jay S. Plugge, Mountain View, all of Calif.

[73] Assignee: Acuson Corporation, Mountain View, Calif.

[21] Appl. No.: 662,330

[22] Filed: Jun. 12, 1996

Related U.S. Application Data

[63] Continuation of Ser. No. 398,348, Mar. 3, 1995, Pat. No. 5,582,177.

[51] Int. Cl.$^{6}$ .................................................. A61B 8/00

[52] U.S. Cl. .................................................. 600/459

[58] Field of Search .................. 128/662.03, 662.04; 310/320, 322, 334, 335, 365, 366, 367, 369; 73/620, 621, 624, 625, 629, 633, 642; 600/459, 472

[56] References Cited

U.S. PATENT DOCUMENTS

| | | |
|---|---|---|
| 2,486,916 | 11/1949 | Bottom . |
| 3,028,752 | 4/1962 | Bacon . |
| 3,666,979 | 5/1972 | McElroy . |
| 3,694,677 | 9/1972 | Guttwein et al. . |
| 3,833,825 | 9/1974 | Haan . |
| 3,936,791 | 2/1976 | Kossoff . |
| 3,968,680 | 7/1976 | Vopilkin et al. . |
| 4,016,751 | 4/1977 | Kossoff . |
| 4,044,273 | 8/1977 | Kanda et al. . |
| 4,084,582 | 4/1978 | Nigam . |
| 4,184,094 | 1/1980 | Kopel . |
| 4,205,686 | 6/1980 | Harris et al. . |
| 4,252,022 | 2/1981 | Hurwitz . |
| 4,276,491 | 6/1981 | Daniel . |
| 4,317,059 | 2/1982 | Besson . |
| 4,350,917 | 9/1982 | Lizzi et al. . |

(List continued on next page.)

FOREIGN PATENT DOCUMENTS

| | | |
|---|---|---|
| 0 145 429 | 6/1985 | European Pat. Off. . |
| 285 482 | 10/1988 | European Pat. Off. . |
| 0 346 891 | 12/1989 | European Pat. Off. . |
| 25 0 8023 | 8/1975 | Germany . |
| 56-57391 | 5/1981 | Japan . |
| 2 079 456 | 1/1982 | United Kingdom . |
| 2 079 102 | 2/1982 | United Kingdom . |
| 2 190 818 | 11/1987 | United Kingdom . |

OTHER PUBLICATIONS

Urick, "Principles of Underwater Sound" McGraw-Hill, New York, New York, 1975.

Schrope, B. et al., "Stimulated Capillary Blood Flow Measurement Using a Nonlinear Contrast Agent," Ultrasonic Imaging, vol. 14, No. 2, pp. 134–158, Apr. 1, 1992.

Barthe, P.G. et al. "A Staircase Model of Tapered-Thickness Piezoelectric Ceramics" Journal of the Acoustical Society of America, vol. 89, No. 3, Mar. 1, 1991, pp. 1434–1442.

Newnham, "Connectivity and Pizoelectric-Pryoelectric Composites," 1978, pp. 525–536.

Swartz, R. et al. "Generation with $PVF_2$," IEEE Trans. vol. SU-27 #6 Nov. 1980 pp. 295–303.

*Primary Examiner*—George Manuel
*Attorney, Agent, or Firm*—Brinks, Hofer, Gilson & Lione

[57] ABSTRACT

There is provided a transducer array with a plurality of piezoelectric elements having a minimum and maximum thickness. In one embodiment, the maximum thickness is less than or equal to 140 percent of the minimum thickness. In an alternate embodiment, the maximum thickness is greater than 140 percent of the minimum thickness and the transducer array is capable of simulating the excitation of a wider aperture two-dimensional transducer array. One or more matching layers may be used to further increase bandwidth performance. In addition, a two crystal transducer element as well as a composite transducer structure may be formed using the principles of this invention.

29 Claims, 8 Drawing Sheets

U.S. PATENT DOCUMENTS

| | | | |
|---|---|---|---|
| 4,398,539 | 8/1983 | Proudian . | |
| 4,412,544 | 11/1983 | Beretsky et al. . | |
| 4,424,465 | 1/1984 | Ohigashi et al. . | |
| 4,437,348 | 3/1984 | Sasaki . | |
| 4,440,025 | 4/1984 | Hayakawa et al. . | |
| 4,445,380 | 5/1984 | Kaminski . | |
| 4,447,715 | 5/1984 | Brisken et al. . | |
| 4,478,085 | 10/1984 | Saski . | |
| 4,485,321 | 11/1984 | Klicker et al. . | |
| 4,507,582 | 3/1985 | Glenn . | |
| 4,518,889 | 5/1985 | Hoen . | |
| 4,523,122 | 6/1985 | Tone et al. . | |
| 4,534,221 | 8/1985 | Fife et al. . | |
| 4,537,074 | 8/1985 | Dietz . | |
| 4,543,293 | 9/1985 | Nakamura et al. . | |
| 4,549,533 | 10/1985 | Cain et al. . | |
| 4,611,141 | 9/1986 | Hamada et al. . | |
| 4,659,956 | 4/1987 | Trzaskos et al. . | |
| 4,699,150 | 10/1987 | Kawabuchi et al. . | |
| 4,794,929 | 1/1989 | Maerfeld . | |
| 4,866,683 | 9/1989 | Phillips . | |
| 4,869,768 | 9/1989 | Zola . | |
| 4,870,972 | 10/1989 | Maerfield et al. . | |
| 4,907,573 | 3/1990 | Nagasaki . | |
| 4,917,096 | 4/1990 | Engelhart . | |
| 4,963,782 | 10/1990 | Bui et al. . | |
| 5,025,790 | 6/1991 | Dias . | |
| 5,101,133 | 3/1992 | Schafer . | |
| 5,111,805 | 5/1992 | Jaggy et al. . | |
| 5,115,809 | 5/1992 | Saitoh . | |
| 5,115,810 | 5/1992 | Watanabe . | |
| 5,193,527 | 3/1993 | Schafer . | |
| 5,291,090 | 3/1994 | Dias . | |
| 5,415,175 | 5/1995 | Hanafy et al. | 128/662.03 |
| 5,423,220 | 6/1995 | Finsterwald et al. | 73/642 |

FIG. 7
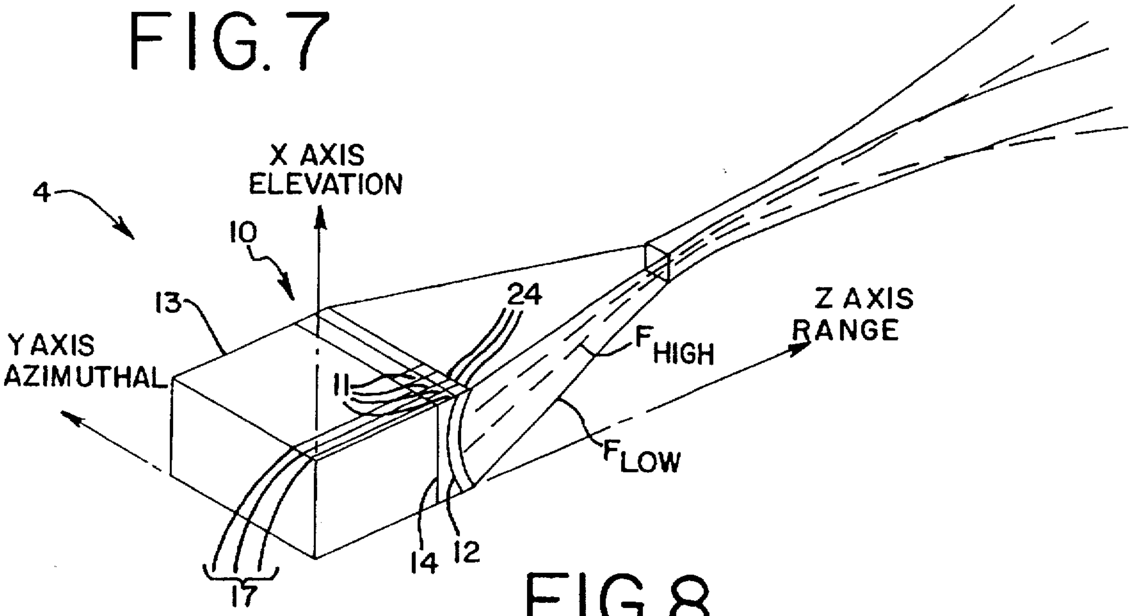
FIG. 8
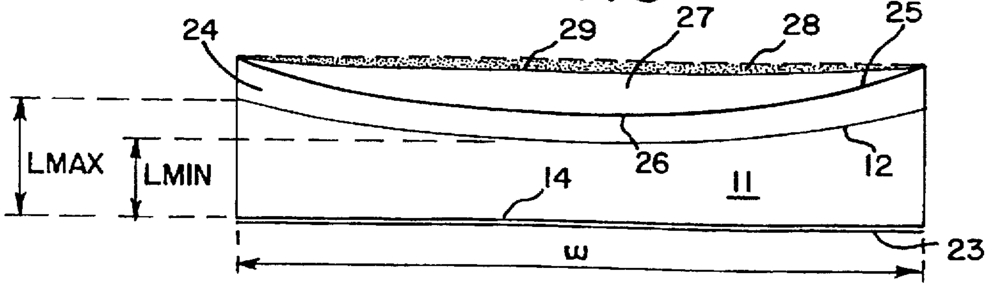
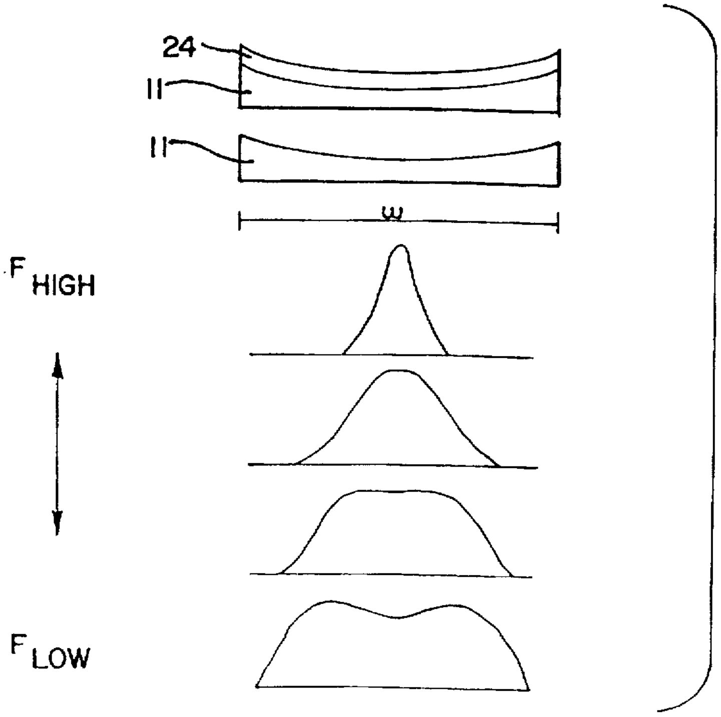
FIG. 9

BROADBAND PHASED ARRAY TRANSDUCER DESIGN WITH FREQUENCY CONTROLLED TWO DIMENSION CAPABILITY AND METHODS FOR MANUFACTURE THEREOF

This application is a continuation of application Ser. No. 08/398,348, filed Mar. 3, 1995, now U.S. Pat. No. 5,582,177.

BACKGROUND OF THE INVENTION

This invention relates to transducers and more particularly to broadband phased array transducers for use in the medical diagnostic field.

Ultrasound machines are often used for observing organs in the human body. Typically, these machines contain transducer arrays for converting electrical signals into pressure waves. Generally, the transducer array is in the form of a hand-held probe which may be adjusted in position to direct the ultrasound beam to the region of interest. Transducer arrays may have, for example, 128 transducer elements for generating an ultrasound beam. An electrode is placed at the front and bottom portion of the transducer elements for individually exciting each element, generating pressure waves. The pressure waves generated by the transducer elements are directed toward the object to be observed, such as the heart of a patient being examined. Each time the pressure wave confronts tissue having different acoustic characteristics, a wave is reflected backward. The array of transducers may then convert the reflected pressure waves into corresponding electrical signals. An example of a previous phased array acoustic imaging system is described in U.S. Pat. No. 4,550,607 granted Nov. 5, 1985 to Maslak et al. and is incorporated herein by reference. That patent illustrates circuitry for combining the incoming signals received by the transducer array to produce a focused image on the display screen.

Broadband transducers are transducers capable of operating at a wide range of frequencies without a loss in sensitivity. As a result of the increased bandwidth provided by broadband transducers, the resolution along the range axis may improve, resulting in better image quality.

One possible application for a broadband transducer is contrast harmonic imaging. In contrast harmonic imaging, contrast agents, such as micro-balloons of protein spheres, are safely injected into the body to illustrate how much of a certain tissue, such as the heart, is active. These micro-balloons are typically one to five micrometers in diameter and, once injected into the body, may be observed via ultrasound imaging to determine how well the tissue being examined is operating. Contrast harmonic imaging is an alternative to Thallium testing where radioactive material is injected into the body and observed by computer generated tomography. Thallium tests are undesirable because they employ potentially harmful radioactive material and typically require at least an hour to generate the computer image. This differs from contrast harmonic imaging in that real-time ultrasound techniques may be used in addition to the fact that safe micro-balloons are employed.

In B. Schrope et al., "Simulated Capillary Blood Flow Measurement Using a Nonlinear Ultrasonic Contrast Agent," *Ultrasonic Imaging*, Vol. 14 at 134–58 (1992), which is incorporated herein by reference, Schrope discloses that an observer may clearly see the contrast agents at the second operating harmonic. That is, at the fundamental harmonic, the heart and muscle tissue is clearly visible via ultrasound techniques. However, at the second harmonic, the observer is capable of clearly viewing the contrast agent itself and thus may determine how well the respective tissue is performing.

Because contrast harmonic imaging requires that the transducer be capable of operating at a broad range of frequencies (i.e. at, both the fundamental and second harmonic), existing transducers typically cannot function at such a broad range. For example, a transducer having a center frequency of 5 Megahertz and having a 70% ratio of bandwidth to center frequency has a bandwidth of 3.25 Megahertz to 6.75 Megahertz. If the fundamental harmonic is 3.5 Megahertz, then the second harmonic is 7.0 Megahertz. Thus, a transducer having a center frequency of 5 Megahertz would not be able to adequately operate at both the fundamental and second harmonic.

In addition to having a transducer which is capable of operating at a broad range of frequencies, two-dimensional transducer arrays are also desirable to increase the resolution of the images produced. An example of a two-dimensional transducer array is illustrated in U.S. Pat. No. 3,833,825 to Haan issued Sep. 3, 1974 and is incorporate herein by reference. Two-dimensional arrays allow for increased control of the excitation of ultrasound beams along the elevation axis, which is otherwise absent from conventional single-dimensional arrays. However, two-dimensional arrays are also difficult to fabricate because they typically require that each element be cut into several segments along the elevation axis, connecting leads for exciting each of the respective segments. A two-dimensional array having 128 elements in the azimuthal axis, for example, would require at least 256 segments, two segments in the elevation direction, as well as interconnecting leads for the segments. In addition, they require rather complicated software in order to excite each of the several segments at appropriate times during the ultrasound scan because there would be at least double the amount of segments which would have to be individually excited as compared with a one-dimensional array.

Further, typical prior art transducers having parallel faces relative to the object being examined tend to produce undesirable reflections at the interface between the transducer and object being examined, producing what is called a "ghost echo." These undesirable reflections may result in a less clear image being produced.

SUMMARY OF THE INVENTION

Consequently, it is a primary objective of this invention to provide a broadband transducer array for use in an acoustic imaging system that is easier and less expensive to manufacture.

It is also an objective of this invention to provide a broadband transducer array capable for use in contrast harmonic imaging.

It is another objective of the present invention to provide a transducer element and a matching layer both having a negative curvature to allow for additive focusing in the field of interest.

It is also an objective of the present invention to provide a transducer array for use in an acoustic imaging system that is capable of simulating a two-dimensional transducer array at least at lower frequencies.

It is a further objective of the present invention to better suppress the generation of undesirable reflections at the surface of the object being examined.

It is another objective of the present invention to further increase the sensitivity and bandwidth of the transducer by disposing one or more matching layers on the front portion of a piezoelectric layer that is facing a region of examination.

To achieve the above objectives, there are provided several preferred embodiments of the present invention. In a first embodiment of this invention, an array-type ultrasonic transducer comprises a plurality of transducer elements disposed adjacent to one another. Each of the elements comprises a front portion facing a region of examination, a back portion, two side portions, and a transducer thickness between the front and back portions. The transducer thickness is a maximum thickness at the side portions and a minimum thickness between the side portions. Further, the maximum thickness is less than or equal to 140 percent of the minimum thickness. Variation in thickness of the element along the range axis as much as 20 to 40 percent is preferred in this embodiment resulting in increased bandwidth and shorter pulse width (i.e., the maximum thickness is between 120 and 140 percent the value of the minimum thickness). This provides improved resolution along the range axis.

In a second embodiment of this invention, a transducer for producing an ultrasonic beam upon excitation comprises a plurality of piezoelectric elements. Each of the elements comprises a thickness at at least a first point on a surface facing a region of examination being less than a thickness at at least a second point on the surface, the surface being generally non-planar. In addition, the aperture of an ultrasound beam produced by the present invention varies inversely as to a frequency of excitation of the element. Generally, where the maximum thickness of the piezoelectric element is greater than 140 percent of the minimum thickness of the piezoelectric element, the transducer may simulate the beam produced by a two-dimensional array at lower frequencies. This is due to the fact that at lower frequencies, the exiting pressure wave generated by the transducer has at least two peaks. Further, the full aperture is typically activated at lower frequencies. Consequently, the second embodiment simulates the excitation of a wider aperture two-dimensional transducer array.

In a third preferred embodiment, a two crystal transducer element design is provided comprising a first piezoelectric portion with a thickness at at least one point on a first surface facing a region of examination being less than a thickness at at least one other point on the first surface, the first surface being generally non-planar. An interconnect circuit may be disposed between the first piezoelectric portion and a second piezoelectric portion. A matching layer may be disposed on the first piezoelectric portion.

In a fourth preferred embodiment, a composite structure transducer is provided comprising a plurality of vertical posts of piezoelectric material comprising varying thickness and polymer layers in between the posts. This structure may be deformed to produce the desired transducer configuration. In addition, a matching layer may be disposed on the composite transducer structure to further increase performance.

The transducer of all embodiments allows for the transducer to operate at a broader range of frequencies and allows for correct apodization. Because the embodiments do not require matching the back acoustic port of the element, they generally are easier to fabricate than prior art devices.

A first preferred method of the invention for making a transducer is disclosed by forming a plurality of transducer elements disposed adjacent to one another. Each of the elements comprises a front portion facing a region of examination, a back portion, two side portions, and a transducer thickness between the front and back portions. Further, the transducer thickness is a maximum thickness at the side portions and a minimum thickness between the side portions, the maximum thickness being less than or equal to 140 percent of the minimum thickness. An electric field is established through at least one portion of each of the elements.

A second preferred method of the invention for making a transducer is disclosed by forming a plurality of piezoelectric elements, each of the elements comprising a thickness at at least one point on a front surface facing a region of examination being less than a thickness at at least one other point on the surface, the surface being generally non-planar. An electric field is established at least through one portion of each of the elements. For example, electrodes may be placed on the front surface and back portion of each of the piezoelectric elements to provide the electric field. Upon application of an excitation pulse to the electrodes, the aperture of an ultrasound beam produced by the transducer varies inversely as to the frequency of the excitation pulse, where the maximum thickness of the piezoelectric element is typically greater than 140 percent of the minimum thickness of the piezoelectric element.

A third preferred method of the invention for making a transducer is disclosed by forming a piezoelectric element comprising composite material comprising a front portion racing a region of examination, the thickness of at least one point on the front portion being less than the thickness on at least one other point on the front portion. First and second electrodes may also be placed on the piezoelectric element. The element may be deformed to the desired shape.

The transducer of all embodiments as well as those made by the disclosed methods may be in the form of a hand-held probe which may be adjusted in position during excitation to direct the ultrasound beam to the region of interest. Further, the transducer of all embodiments as well as those made by the disclosed methods may be placed in a housing for placement in a hand-held probe. Other types of probes and manners of directing the beam are possible. The ultrasound system for generating an image comprises transmit circuitry for transmitting electrical signals to the transducer probe, receive circuitry for processing the signals received by the transducer probe, and a display for providing the image of the object being observed. The transducers convert the electrical signals provided by the transmit circuitry to pressure waves and convert the pressure waves reflected from the object being observed into corresponding electrical signals which are then processed in the receive circuitry and ultimately displayed.

BRIEF DESCRIPTION OF THE DRAWINGS

FIG. 7 is a perspective view of a broadband transducer array in accordance with the present invention further illustrating the probe of FIG. 1 and having a curved matching layer disposed on a front portion of the transducer elements.

FIG. 8 is a cross-sectional view of a single broadband transducer element in accordance with the present invention having a curved matching layer and further having a coupling element thereon.

FIG. 9 is a view of the exiting beam width produced by the broadband transducer elements from low to high frequencies as compared to the width of the transducer element in accordance with the second preferred embodiment.

DESCRIPTION OF THE PREFERRED EMBODIMENTS

Figure 1:
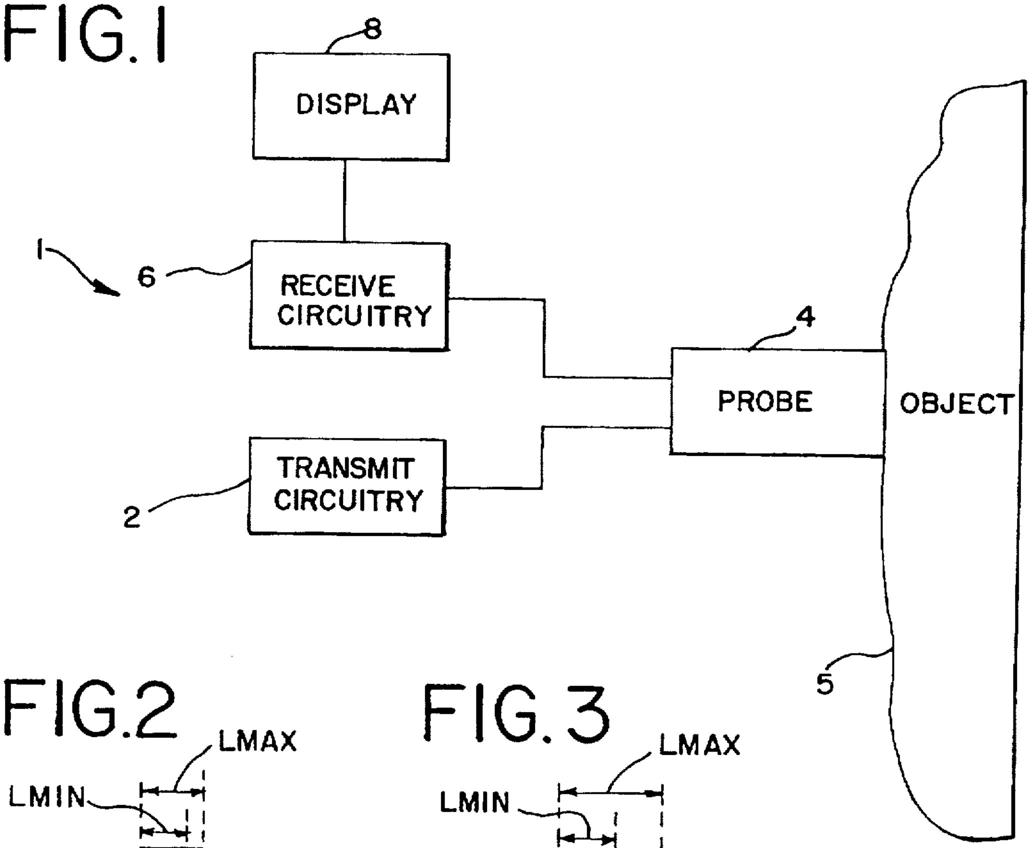
FIG. 1 is a schematic view of an ultrasound system for generating an image.

Referring now to the accompanying drawing FIG. 1, there is provided a schematic view of an ultrasound system 1 for generating an image of an object or body 5 being observed. The ultrasound system 1 has transmit circuitry 2 for transmitting electrical signals to the transducer probe 4, receive circuitry 6 for processing the signals received by the transducer probe, and a display 8 for providing the image of the object 5 being observed.

Figure 4:
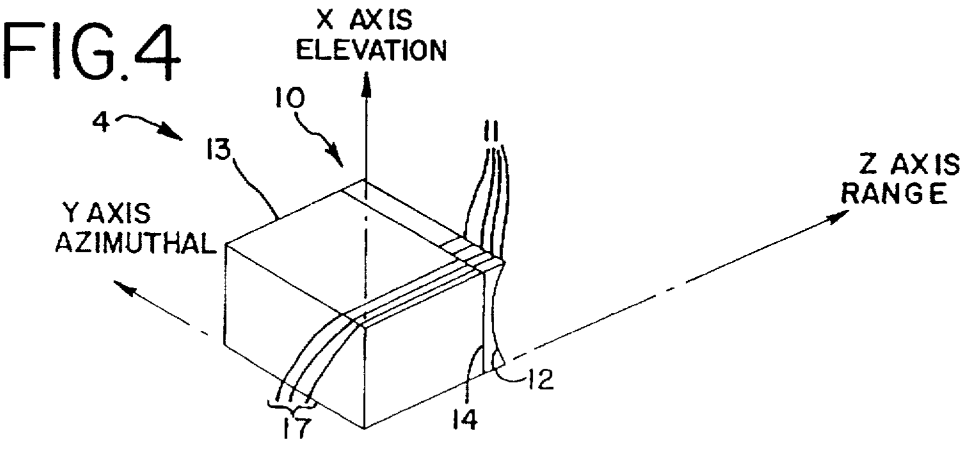
FIG. 4 is a perspective view of a broadband transducer array further illustrating the probe of FIG. 1 in accordance with the first preferred embodiment.

Referring also to FIG. 4, the probe 4 contains an array 10 of transducer elements 11. Typically, there are one hundred twenty eight elements 11 in the y-azimuthal axis forming the broadband transducer array 10. However, the array can consist of any number of transducer elements 11 each arranged in any desired geometrical configuration. The transducer array 10 is supported by backing block 13.

The probe 4 may be hand-held and can be adjusted in position to direct the ultrasound beam to the region of interest. The transducer elements 11 convert the electrical signals provided by the transmit circuitry 2 to pressure waves. The transducer elements 11 also convert the pressure waves reflected from the object 5 being observed into corresponding electrical signals which are then processed in the receive circuitry 6 and ultimately displayed 8.

Figure 2:
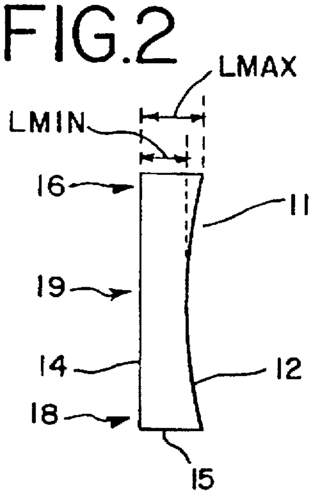
FIG. 2 is a cross-sectional view of a transducer element in accordance with the first preferred embodiment.
Figure 6:
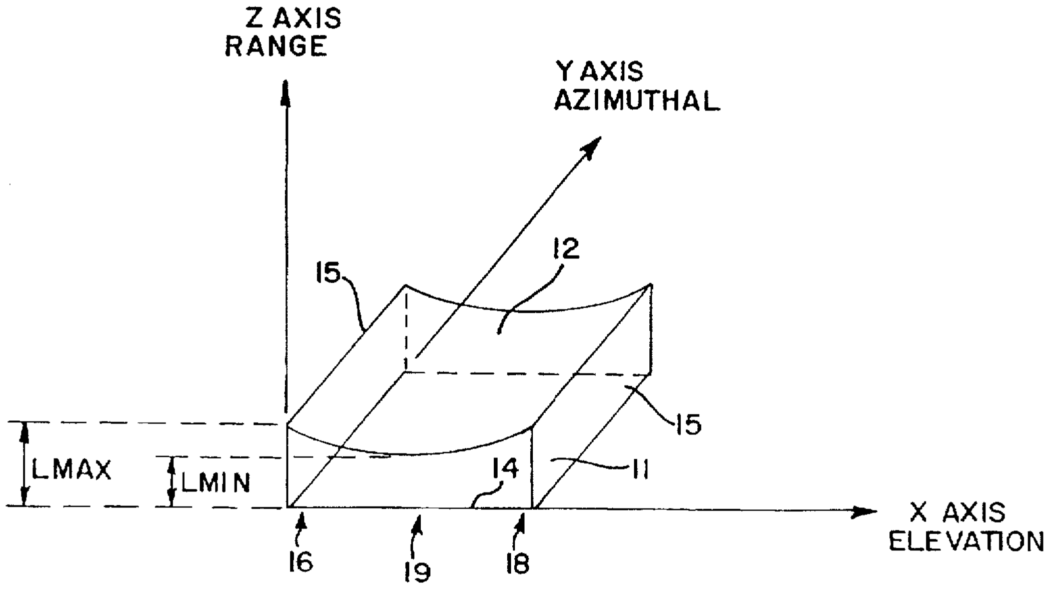
FIG. 6 is an enlarged view of a single broadband transducer element of the transducer array constructed in accordance with the present invention.

Referring to FIGS. 2, 4, and 6, there is provided the first embodiment of the present invention. Transducer element 11 has a front portion 12, a back portion 14, a center portion 19, and two side portions 16 and 18. The front portion 12 is the surface which is positioned toward the region of examination. The back portion 14 may be shaped as desired, but is generally a planar surface. The front portion 12 is generally a non-planar surface, the thickness along the z-axis of element 11 may be greater at each of the side portions 16 and 18 and smaller between the side portions. The term side portion 16, 18 refers not only to the sides 15 of the respective element 11, but may also include a region interior to the element 11 where the thickness of the element is greater than a thickness toward the interior of the element (e.g., where the thickness of each of the sides of the element are tapered).

Although the front portion 12 is illustrated having a continuously curved surface, front portion 12 may include a stepped configuration, a series of linear segments, or any other configuration wherein the thickness of element 11 is greater at each of the side portions 16 and 18 and decreases in thickness at the center portion 19, resulting in a negatively "curved" front portion 12. The back portion 14 which is generally preferably a planar surface may also be, for example, a concave or convex surface.

Element 11 has a maximum thickness LMAX and a minimum or smallest thickness LMIN, measured along the range axis. Preferably the side portions 16 and 18 both are equal to the thickness LMAX and the center of element 11, or substantially near the center of element 11, is at the thickness of LMIN. However, each of the side portions 16, 18 do not have to be the same thickness and LMIN does not have to be in the exact center of the transducer element to practice the invention.

In the first preferred embodiment, the value of LMAX is less than or equal to 140 percent the value of LMIN. This allows for an increase in bandwidth activation energy generally without the need to reprogram the ultrasound machine for generating the ultrasound beam. Further, when the value of LMAX is less than or equal to 140 percent the value of LMIN, the exiting beam width is generally the same for different exciting frequencies.

The increase in bandwidth activation energy for the transducer configuration of the present invention is approximated by LMAX/LMIN where the transducer is of the free resonator type (i.e., does not comprise a matching layer) or is an optimally matched transducer (i.e., has at least two matching layers), to be discussed later. In the first preferred embodiment shown in FIGS. 2, 4, and 6, the bandwidth may be increased by 40 percent by increasing the thickness of LMAX relative to LMIN by 40 percent, respectively (e.g., LMAX is 140 percent of the value of LMIN).

If, for example, a transducer has an LMAX of 0.3048 mm and an LMIN of 0.254 mm, the bandwidth is increased by 20 percent as compared to a transducer having a uniform thickness of 0.254 mm. Similarly, if a transducer has an LMAX of 0.3556 mm and an LMIN of 0.254 mm, the bandwidth is increased by 40 percent as compared to a transducer having a uniform thickness of 0.254 mm. Variation in thickness of the element along the range axis as much as 20 to 40 percent is preferred in this embodiment resulting in increased bandwidth and shorter pulse width (i.e., the maximum thickness is greater than or equal to 120 percent of the minimum thickness or less than or equal to 140 percent of the minimum thickness). This results in the maximum bandwidth increase, approximately 20 to 40 percent, respectively. Further, this provides improved resolution along the range axis.

The slight variation in thickness of the front portion 12 relative to the back portion 14 of the first embodiment allows for better transducer performance where, for example, the transducer is activated at three different frequencies, such a 2 MHz, 2.5 MHz, and 3 MHz, known as a tri-frequency mode of operation. Such a tri-frequency mode of operation may be used in cardiac applications. Moreover, the slight variation in transducer thickness may also improve transducer performance for other tri-frequency modes of operation, such as operation at the frequencies of 2.5 MHz, 3.5 MHz, and 5 MHz.

Preferably, the element 11 is a plano-concave structure and is composed of the piezoelectric material lead zirconate titanate (PZT). However, the element 11 may also be formed of composite material as discussed later, polyvinylidene fluoride (PVDF), or other suitable material. Referring also to FIG. 8, electrodes 23 and 25 may appropriately be placed on the front 12 and bottom 14 portions of the element 11 in order to excite the element to produce the desired beam, as is well known in the art. Although electrode 25 is shown to be disposed directly on the piezoelectric element 11, it may alternatively be disposed on matching layer 24. As a result, the matching layer 24 may be directly disposed on piezoelectric element 11. The electrodes 23 and 25 establish an electric field through the element 11 in order to produced the desired ultrasound beam.

An example of the placement of electrodes in relation to the piezoelectric material is illustrated in U.S. Pat. No. 4,611,141 to Hamada et al. issued Sep. 9, 1986 and is incorporated herein by reference. A first electrode 23 provides the signal for exciting the respective transducer element and the second electrode may be ground. Leads 17 may be utilized to excite each of the first electrodes 23 on the respective transducer elements 11 and the second electrodes 25 may all be connected to an electrical ground. As is commonly known in the industry, electrodes may be disposed on the piezoelectric layer by use of sputtering techniques. Alternatively, an interconnect circuit, described later, may be used to provide the electrical excitation of the respective transducer elements.

Figure 3:
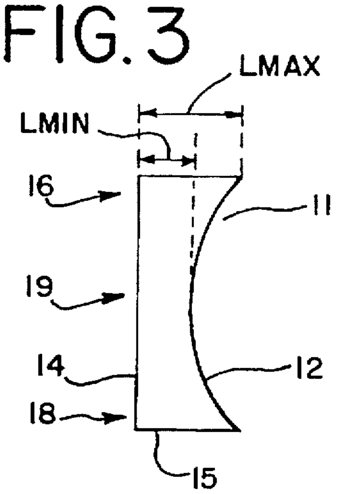
FIG. 3 is a cross-sectional view of a transducer element in accordance with the second preferred embodiment.
Figure 5:
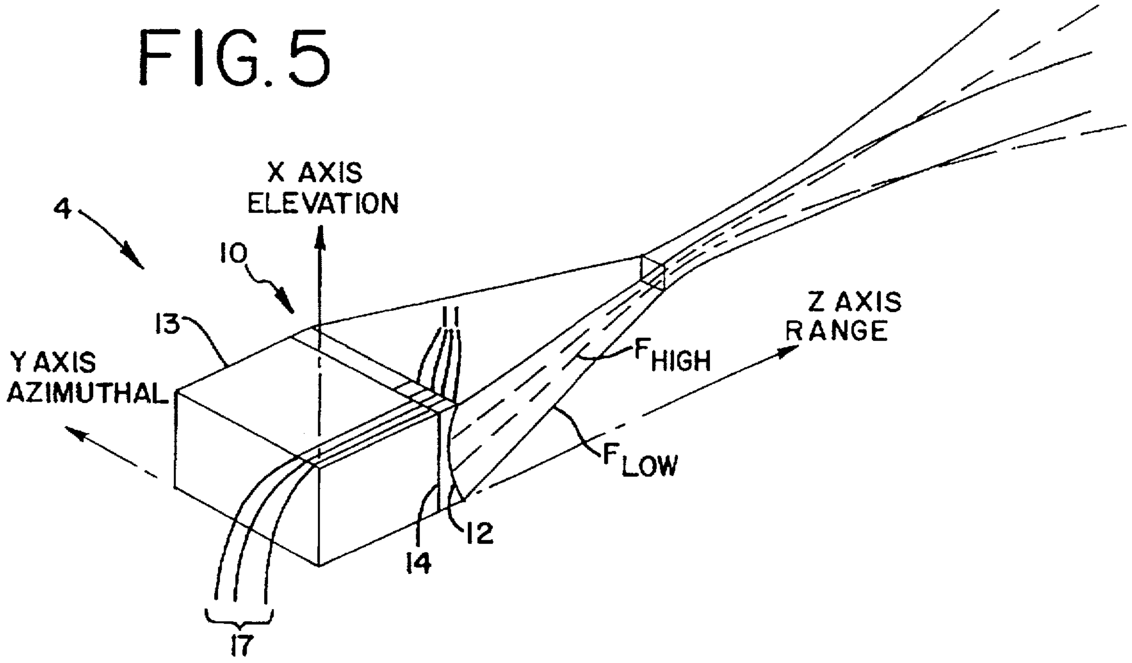
FIG. 5 is a perspective view of a broadband transducer array further illustrating the probe of FIG. 1 and the beam widths produced for low and high frequencies in accordance with the second preferred embodiment.

Referring now to FIGS. 3 and 5, there is shown the second preferred embodiment of the present invention wherein like components have been labeled similarly. Although FIGS. 6 and 8 have been described in relation to the first preferred embodiment, they will be used to illustrate the second preferred embodiment in light of the similarity of the two embodiments. Further, the thickness at at least a first point on the front portion 12 is less than a thickness at at least a second point on the front portion. In addition, the front portion is generally non-planar.

In the second preferred embodiment, the value of LMAX is greater than 140 percent the value of LMIN. Where the value of LMAX is greater than 140 percent of the value of LMIN, the exiting beam width produced typically varies with frequency. In addition, the lower the frequency, the wider the exiting beam width.

FIG. 9 illustrates the typical variation in the exiting beam width or aperture along the elevation direction produced by the broadband transducer from low to high frequencies in accordance with the second preferred embodiment. At high frequencies, such as 7 Megahertz, the beam has a narrow aperture. When the frequency is lowered, the beam has a wider aperture. Further, at low enough frequencies, such as 2 Megahertz, the beam is effectively generated from the full aperture of the transducer element 11. As shown in FIG. 9, the exiting pressure wave has two peaks, simulating the excitation of a wide aperture two-dimensional transducer array at lower frequencies.

FIGS. 5 further illustrates the beam width variation of the whole transducer array as a function of frequency for the second preferred embodiment. At high excitation frequencies, the exiting beam width has a narrow aperture and is generated from the center of elements 11. On the contrary, at low excitation frequencies, the exiting beam width has a wider aperture and is generated from the full aperture of elements 11.

By controlling the excitation frequency, the operator may control which section of transducer element 11 generates the ultrasound beam. That is, at higher excitation frequencies, the beam is primarily generated from the center of the transducer element 11 and at lower excitation frequencies, the beam is primarily generated from the full aperture of the transducer element 11. Further, the greater the curvature of the front portion 12, the more the element 11 simulates a wide aperture two-dimensional transducer array.

In order to pursue the second preferred embodiment, that is, increasing the bandwidth greater than 40 percent, it may be necessary to reprogram the ultrasound machine for exciting the transducer at such a broad range of frequencies. As seen by the equation LMAX/LMIN, the greater the thickness variation, the greater the bandwidth increase. Bandwidth increases of 300 percent, or greater, for a given design may be achieved in accordance with the principles of the invention. Thus, the thickness LMAX would be approximately three times greater than the thickness LMIN. The bandwidth of a single transducer element, for example, may range from 2 Megahertz to 11 Megahertz, although even greater ranges may be achieved in accordance with the principles of this invention. Because the transducer array constructed in accordance with this invention is capable of operating at such a broad range of frequencies, contrast harmonic imaging may be achieved with a single transducer array in accordance with this invention for observing both the fundamental and second harmonic (i.e., the transducer is operable at a dominant fundamental harmonic frequency and is operable at a dominant second harmonic frequency).

Figure 10:
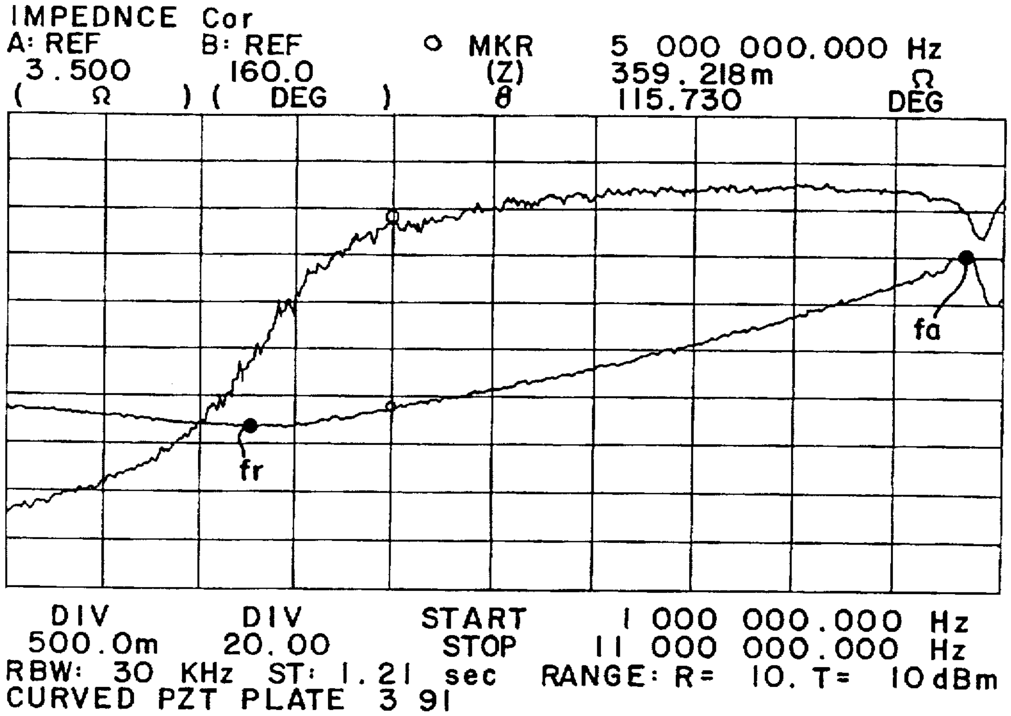
FIG. 10 is an example of a typical acoustic impedance frequency response plot resulting from operation of the transducer constructed in accordance with the second preferred embodiment.
Figure 11:
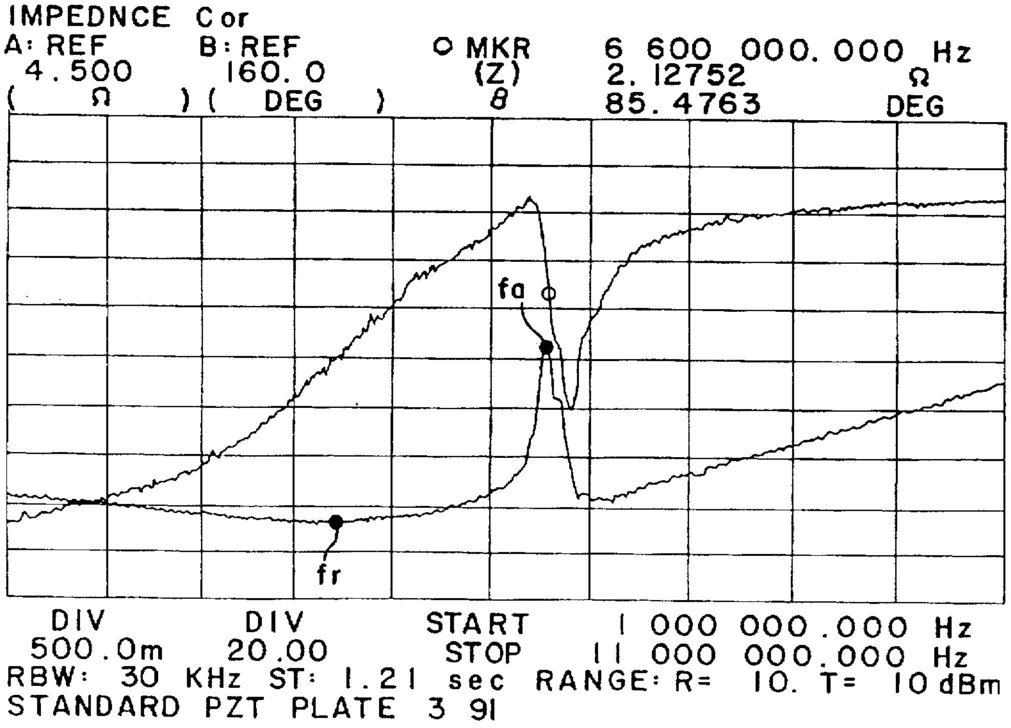
FIG. 11 is an example of a typical acoustic impedance frequency response plot resulting from operation of a prior art transducer.

The thickness variation of the transducer element 11 greatly increases the bandwidth, as illustrated in FIGS. 10 and 11. FIGS. 10 and 11 provide one example of the effect of utilizing a plano-concave transducer element 11 on bandwidth performance and results may vary depending on the particular configuration used. FIG. 10 illustrates an impedance plot for a transducer element 11 produced in accordance with the second preferred embodiment of the present invention having an outer edge thickness LMAX of 0.015 inches (0.381 mm) and a center thickness LMIN of 0.00428 inches (0.109 mm). As can be seen, the element has a bandwidth from approximately 3.5 Megahertz to 10.7 Megahertz. In contrast, a conventional element having a uniform thickness of 0.381 mm typically has a bandwidth of approximately 4.5 Megahertz to approximately 6.6 Megahertz, as illustrated by FIG. 11. Thus, by comparing Δf, which is the difference between $f_a$, the anti-resonant frequency (i.e., maximum impedance), and $f_r$, the resonant frequency (i.e., minimum impedance), a fractional bandwidth of 100% is provided by the transducer element produced in accordance with the present invention versus a fractional bandwidth of approximately 38% for the prior art design.

Therefore, by controlling the curvature shape of the transducer element (i.e., cylindrical, parabolic, gaussian, stepped, or even triangular), one can effectively control the frequency content of the radiated energy. The use of each of these shapes, as well as others, is considered within the scope of the present invention.

Referring now to FIGS. 7 and 8, wherein like components are labeled similarly, the transducer structure in accordance with the invention is shown having a curved matching layer 24 disposed on the front portion 12 of transducer element 11. The matching layer 24 is preferably made of a filled polymer. Moreover, the thickness of the matching layer 24 is preferably approximated by the equation:

$$LML=(\frac{1}{2})(LE)\ (CML/CE)$$

where, for a given point on the transducer surface, LML is the thickness of the matching layer, LE is the thickness of the transducer element, CML is the speed of sound of the matching layer, and CE is the speed of sound of the element. The curvature of the front portion 12 may be different than the curvature of the top portion 26 of the matching layer 24 because the thickness of the matching layer depends on the thickness of the element at a given point of the transducer surface. Although one or more matching layers are preferably formed using the above equation, the matching layers may be constant in thickness for ease of manufacturing.

By the addition of matching layer 24, the fractional bandwidth can be improved. Further, the transducer may act with increased sensitivity. However, the thickness difference between the edge and center of the assembled substrates will control the desired bandwidth increase, and the shape of the curvature will control the base bandshape in the frequency domain. Further, because both the transducer element 11 and the matching layer 24 have a negative curvature, there is additive focusing in the field of interest.

More than one matching layer may be added to the front portion 12 to effect focusing in the field of interest and tò improve the sensitivity of the transducer. Preferably, there are two matching layers placed upon the piezoelectric element 11 resulting in an optimally matched transducer. Each are calculated by the equation LML=(½) (LE) (CML/CE). Specifically, for calculating the thickness LML for the first matching layer, the value of the speed of sound CML for that first material is used. When calculating the thickness LML for the second matching layer, the value of the speed of sound CML for that second material is used. Preferably, the value of the acoustic impedance for the first matching layer (i.e., the matching layer closest to the piezoelectric element) is approximately 10 Mega Rayls and the value of the acoustic impedance for the second matching layer (i.e., the matching layer closest to the object being observed) is approximately 3 Mega Rayls.

A coupling element 27 having the acoustical properties of the object being examined may be disposed on the matching layer or directly on the second electrode 25 if, for example, the matching layer is not used. The coupling element 27 may provide increased patient comfort because it may alleviate any of the sharper surfaces in the transducer structure which are in contact with the body being examined. The coupling element 27 may be used, for example, in applications where the curvature of the front portion 12 or top portion 26 are large. The coupling element 27 may be formed of unfilled polyurethane. The coupling element may have a surface 29 which is generally flat, slightly concave, or slightly convex. Preferably, the curvature of surface 29 is slightly concave so that it may hold an ultrasound gel 23, such as Aquasonic® manufactured by Parker Labs of Orange, N.J., now shown, between the probe 4 and the object being examined. This provides strong acoustical contact between the probe 4 and the object being examined. The matching layer and coupling element described may be placed on all of the embodiments disclosed.

Machines such as a numerically controlled machine tool which is commonly used in the ultrasound industry may be used to provide the thickness variation of the transducer element. The machine tool may machine an initial piezoelectric layer in order to have the desired thickness variation of LMAX and LMIN.

Figure 16:
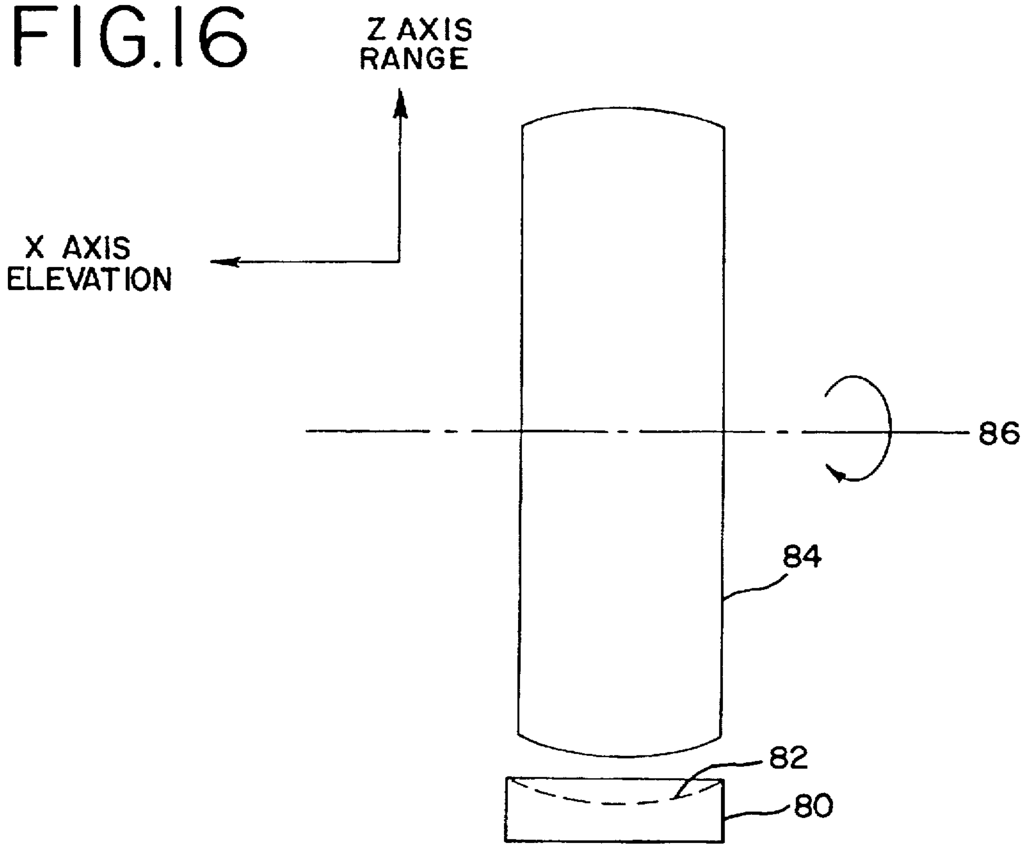
FIG. 16 is a cross-sectional view of a piezoelectric layer and surface grinder wheel illustrating a preferred method for machining the surface of the piezoelectric layer.

FIG. 16 shows a first method of machining the piezoelectric layer 80 where it is desired to have a curvature 82 on the front portion. The numerically controlled machine is first inputted with the coordinates for defining the radius of curvature R approximated by the equation $h/2+(w^2/8h)$, where h is the thickness difference between LMAX and LMIN and w is the width of the transducer element along the elevation axis. Then, a surface grinder wheel 84 on the numerically controlled machine having a width coextensive in size with the piezoelectric layer 80 machines the piezoelectric layer. The surface grinder wheel rotates about an axis 86 which is parallel to the elevation axis. The surface grinder wheel contains an abrasive material such as Aluminum Oxide. The surface grinder wheel preferably begins machining at one end of the piezoelectric layer 80 along the azimuthal direction until it reaches the other end of the piezoelectric layer.

Figure 17:
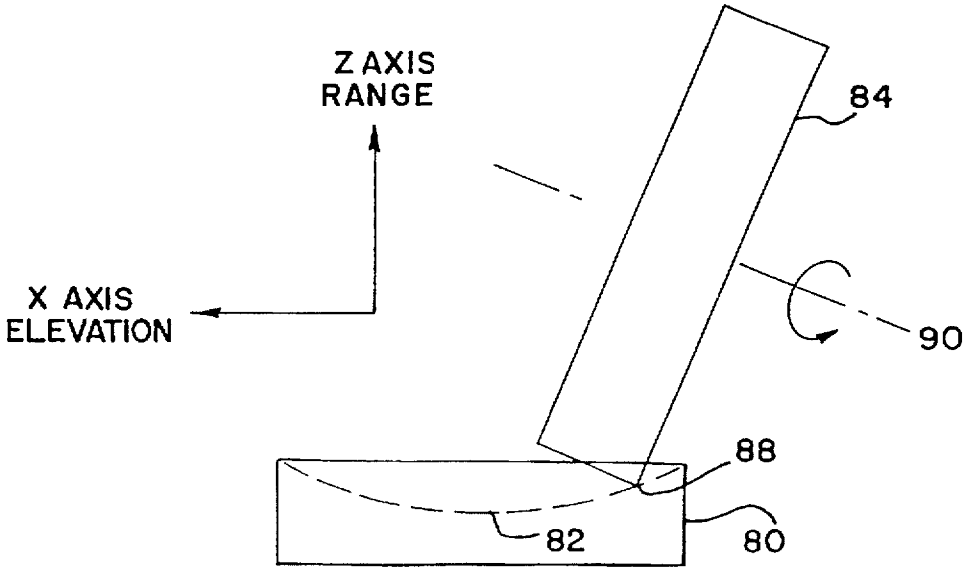
FIG. 17 is a cross-sectional view of a piezoelectric layer and surface grinder wheel illustrating another preferred method for machining the surface of the piezoelectric layer.

FIG. 17 shows an alternate method of machining the piezoelectric layer 80. With this method, the surface grinder wheel 84 is tilted such that one corner 88 of the surface grinder wheel contacts a surface of the piezoelectric layer 80. For a given azimuthal region, the surface grinder wheel 84 begins at one side of the piezoelectric layer 80 along the elevation axis until it reaches the other side of the piezoelectric layer along the elevation axis (e.g., the surface grinder wheel makes the desired cut along the elevation axis for a certain index in the azimuthal axis). The surface grinder wheel 84 rotates about an axis 90. Then, the surface grinder wheel 84 is moved to a different region or index along the azimuthal axis and repeats the machining from one side to the other side of the piezoelectric layer along the elevation axis. This process is repeated until the whole piezoelectric layer 80 is machined to have the desired curvature 82.

The machined surface may also be ground or polished to provide a smooth surface. This is especially desirable where the transducer is used at very high frequencies such as 20 MHz.

Figure 18:
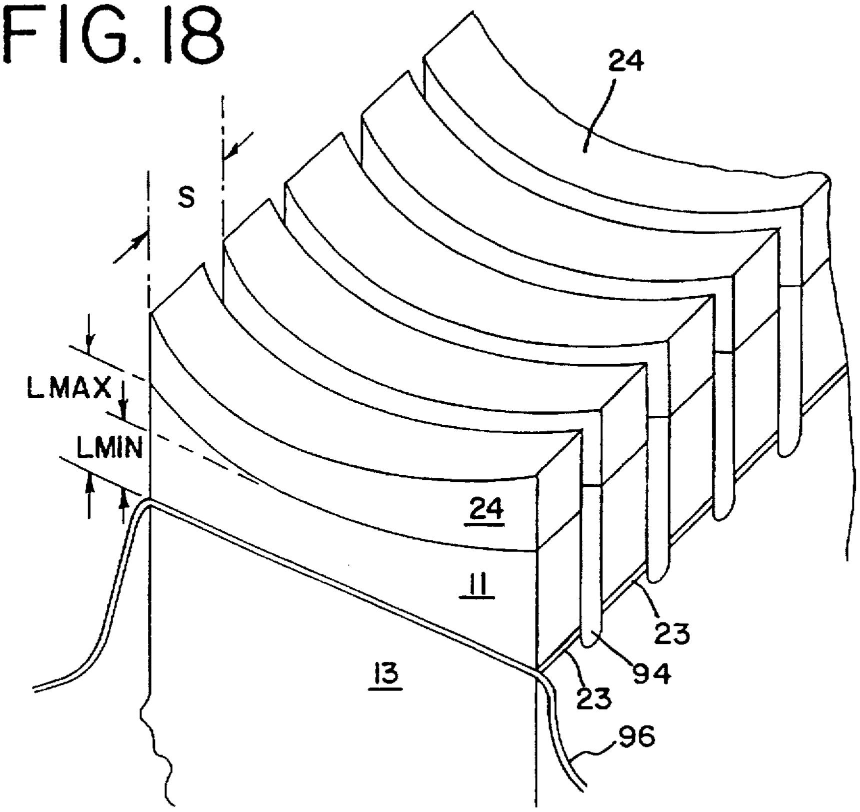
FIG. 18 shows a partial perspective view of a linear transducer array in accordance with the present invention.

Referring also to FIGS. 7 and 18, a number of electrically independent piezoelectric elements 11 may then be formed by dicing kerfs 94 accomplished by dicing the piezoelectric material, as is commonly done in the industry. The kerfs 94 result in a plurality of matching layers 24, piezoelectric elements 11, and electrodes 23. The kerf may also slightly extend into the backing block 13 to ensure electrical isolation between transducer elements.

Referring to FIG. 8, a metalization layer may be directly deposited on top of the piezoelectric layer prior to dicing to form the second electrodes 25. If a matching layer 24 is also employed, the second electrode 25 is preferably disposed on the top portion 26 of matching layer 24. However, the top portion 26 of the matching layer 24 is preferably shorted to the second electrode 25 via metalization across the edges of the matching layer or by using an electrically conductive material such as magnesium or a conductive epoxy. In addition, where a matching layer is used, the dicing may be done after the matching layer is disposed on top of the piezoelectric layer. In a preferred embodiment, the second electrode 25 is held at ground potential. If a flex circuit 96, described later, is used, the dicing may extend through the flex circuit, forming individual electrodes 23.

When the transducer is designed for operation in the sector format, the length S, which is the element spacing along the azimuthal direction, is preferably approximated by half a wavelength of the object being examined at the highest operating frequency of the transducer. This approximation also applies for the two crystal design described later. When the transducer is designed for linear operation, or if the transducer array is curvilinear in form, the value S may vary between one and two wavelengths of the object being examined at the highest operating frequency of the transducer.

Figure 19:
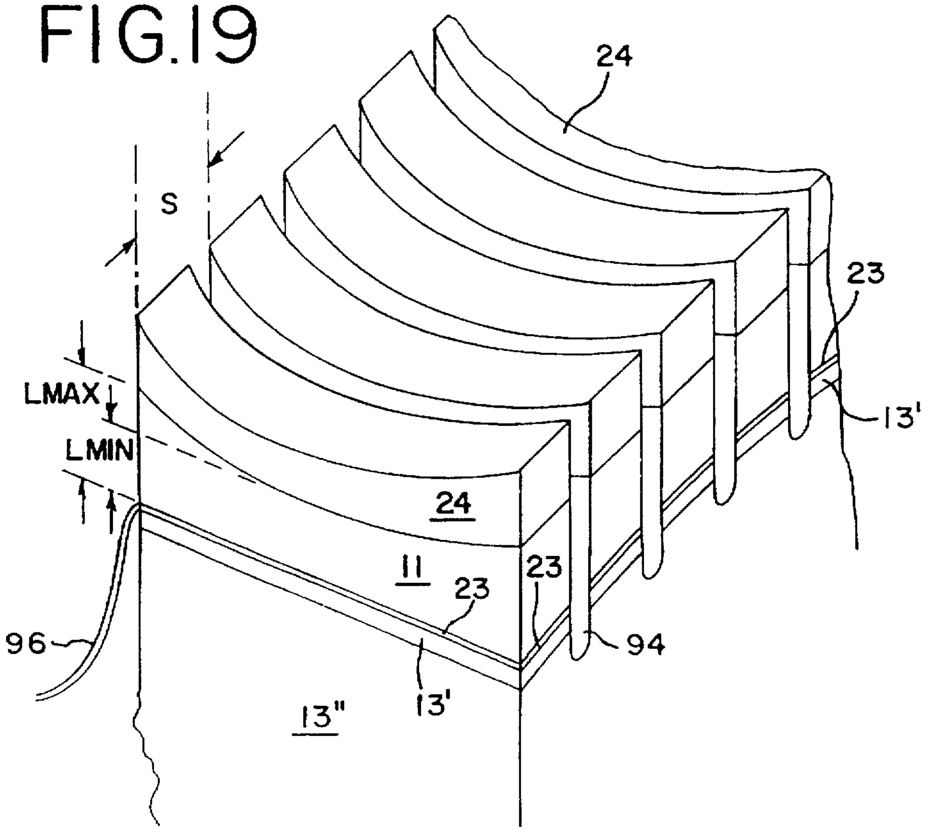
FIG. 19 shows a partial perspective view of a curvilinear transducer array in accordance with the present invention with a portion of the flex circuit removed at one end for purposes of illustration.

FIG. 19 shows a curvilinear transducer array constructed in accordance with the principles of this invention. Specifically, the curvilinear array is constructed similarly to the linear transducer array of FIG. 18. However, rather than directly resting on the large backing block 13 of FIG. 18, the piezoelectric elements 11 and flex circuit 96 with corresponding electrodes 23 are placed directly upon a first backing block 13' having a thickness of approximately 1 mm. This allows easy bending of the array to the desired amount in order to increase the field of view.

Typically, the radius of curvature of the first backing block 13' is approximately 44 mm but may vary as desired. The first backing block may be secured to a second backing block 13" having a thickness in the range direction of approximately 2 cm by use of an epoxy glue. Preferably, the surface of the second backing block 13" adjacent to the first backing block 13' has a similar radius of curvature. As is commonly know in the industry, a curvilinear array functions similarly to a linear array having a mechanical lens disposed in front of the linear array.

Because the signal at the center portion 19 of the transducer element 11 is stronger than at the end or side portions 16 and 18, correct apodization occurs (i.e. reduces or suppresses the generation of sidelobes). This is due to the fact that the electric field between the two electrodes on the front portion 12 and bottom portion 14 is greatest at the center portion 19, reducing side lobe generation. In addition, because the front and bottom portions are not flat parallel surfaces, the generation of undesirable reflections at the interface of the transducer and object being examined (i.e., ghost echoes) are better suppressed. Further, because the transducer array constructed in accordance with the present invention is capable of operating at a broad range of frequencies, the transducer is capable of receiving signals at center frequencies other than the transmitted center frequency.

As to the design of the spacing between the elements 11 and the design of the transducer aperture or width w, the upper operating frequency of a transducer will have the greatest impact on the grating lobe. The grating lobe image artifact (i.e., the creation of undesirable multiple mirror images of the object being observed) can be avoided if one designs the element spacing to take into account the highest operating frequency for the transducer. Specifically, the relationship between the grating lobe angle $\theta_g$, the electronic steering angle in sector format $\theta_s$, the wavelength of the object being examined at the highest operating frequency of the transducer $\lambda$, and the spacing between the elements S is given by the equation:

$$S \leq \lambda/(\sin\theta_s - \sin\theta_g).$$

Therefore, for a given grating lobe angle, the design of the transducer aperture is restricted by the upper operating frequency of the transducer.

As illustrated by the equation, in order to sweep at higher frequencies, it is necessary to reduce the aperture correlating to that frequency. For example, at an operating frequency of 3.5 Megahertz, the desired spacing between the elements S is 220 um while at 7.0 Megahertz, the spacing S is 110 um. Because at higher frequencies it is desirable to decrease the aperture of the transducer element as given by the above described equation, use of the transducer element at lower frequencies will result in some resolution loss. This is due to the fact that lower frequency operation typically requires a greater element aperture. However, this is compensated by the fact that the transducer simulates a two-dimensional array at lower frequencies where the value of LMAX is greater than 140 percent the value of LMIN, which increases the resolution of the images produced at the lower frequencies by wider aperture.

Figure 12:
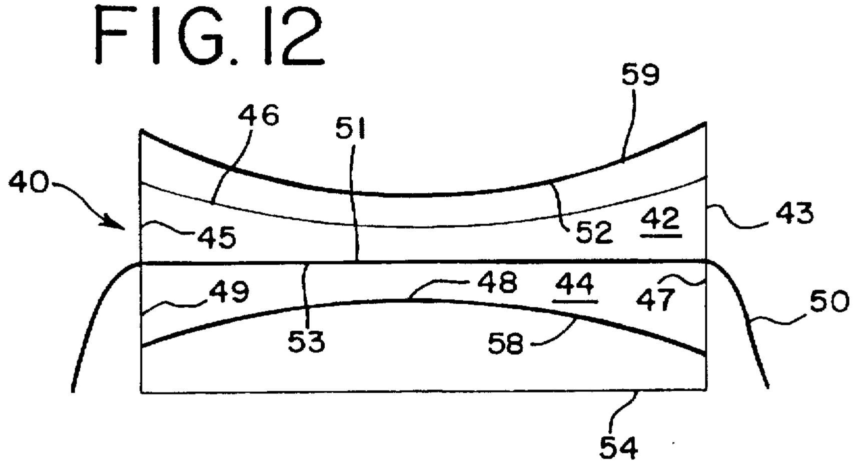
FIG. 12 is a cross-sectional view of a two crystal design having interconnect circuitry between the two crystal elements in accordance with the third preferred embodiment.

A two crystal transducer element design may be employed using the principles of this invention. Referring to FIG. 12, a two crystal transducer element 40 is shown having a first piezoelectric portion 42 and a second piezoelectric portion 44. These piezoelectric portions may be machined as two separate pieces. Preferably, both surfaces 46 and 48 are generated by the equation $h/2+(w^2/8h)$, where h is the thickness difference between LMAX and LMIN and w is the width of the transducer element along the elevation axis. Although piezoelectric portions 42 and 44 are illustrated as being plano-concave in structure, the surfaces 46 and 48 may include a stepped configuration, a series of linear segments, or any other configuration. The thickness of each of the portions 42 and 44 may be greater at each of the side portions 43, 45, 47, 49 and decrease in thickness at the respective center portions of piezoelectric portions 42 and 44. In addition, the back portions 51 and 53 of the piezoelectric portions 42 and 44, respectively, are preferably generally planar surfaces. However, these surfaces may also be non-planar.

An interconnect circuit 50 is disposed between the first piezoelectric portion 42 and the second piezoelectric portion 44. The interconnect circuit 50 may comprise any interconnecting design used in the acoustic or integrated circuit fields. The interconnect circuit 50 is typically made of a copper layer carrying a lead for exciting the transducer element 40. The copper layer may be bonded to a piece of polyamide material, typically kapton. Preferably, the copper layer is coextensive in size with each of the piezoelectric portions 42 and 44. In addition, the interconnect circuit may be gold plated to improve the contact performance. Such an interconnect circuit may be a flex circuit manufactured by Sheldahl of Northfield, Minnesota.

To further increase performance, a matching layer 52 may be disposed above piezoelectric portion 42. Where both the first and second piezoelectric portions are formed of the same material, the matching layer 52 has a matching layer thickness LML approximated by (½) (LE) (CML/CE), where, for a given point on the transducer surface, LML is the thickness of the matching layer, LE is the thickness of the first and second piezoelectric portions, CML is the speed of sound of the matching layer, and CE is the speed of sound of the piezoelectric portions. Ground layers 58 and 59 may be disposed directly on the matching layer 52 and on surface 48, connecting the two piezoelectric portions in parallel.

The matching layer may be coated with electrically conductive material, such as nickel and gold. However, if the matching layer 52 is not employed, then the ground layers are both disposed directly on the piezoelectric portions 42 and 44. The matching layer 52 may face the region being examined. The transducer 40 may be placed on a backing block 54, as is commonly used in the ultrasonic field. Further, a coupling element as described earlier may also be used.

Figure 13:
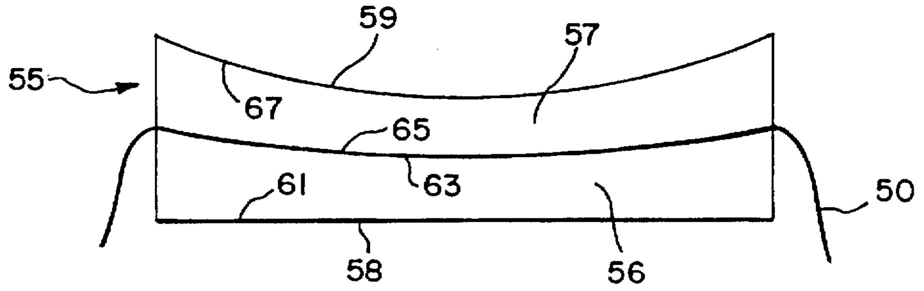
FIG. 13 is a cross-sectional view of an alternate two crystal design.

FIG. 13 illustrates another two crystal design 55 employing the principles of this invention. A first piezoelectric portion 56 and a second piezoelectric portion 57 are provided. The piezoelectric portion 56 is preferably plano-concave in shape. In addition, the second piezoelectric portion 57 has a thickness variation along the elevation direction as well. An interconnect circuit 50 as described above may be used in between the two piezoelectric portions to excite the two crystal transducer 55. A matching layer as well as a coupling element as described earlier may also be provided to improve performance as well as patient comfort. Further, electrodes 58 and 59 may be used to connect the two piezoelectric portions in parallel.

Preferably, the back portion 61 of the first piezoelectric portion 56 is generally a flat surface. The radius of curvature R for the front portion 63 and the bottom portion 65 of the first and second piezoelectric portions 56 and 57, respectively, is approximated by the equation $h/2+(w^2/8h)$, where h is the thickness difference between LMAX and LMIN of piezoelectric portion 56 and w is the width of the transducer element along the elevation axis. Preferably, the value of LMAX and LMIN is the same for both the first and second piezoelectric portions 56 and 57. The radius of curvature R for the front portion 67 of the second piezoelectric portion 57 is approximated by the equation $h'/2+(w^2/8h')$, where h' is the thickness difference between the combined maximum thickness for both piezoelectric portions and the combined minimum thickness for both piezoelectric portions and w is the width of the transducer element along the elevation axis. To achieve the desired radii of curvature, piezoelectric portions 56 and 57 may be machined by a numerically controlled machine tool as described earlier.

Figure 14:
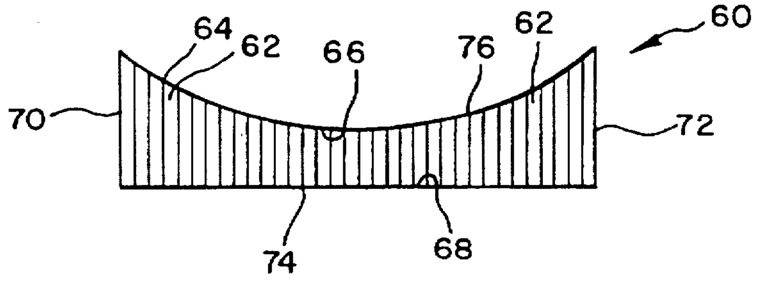
FIG. 14 is a cross-sectional view of a composite transducer element in accordance with a fourth preferred embodiment.

Instead of using a uniform layer of piezoelectric material, a composite structure 60 as shown in FIG. 14 may be utilized formed of composite material. The composite structure 60 contains a plurality of vertical posts or slabs of piezoelectric material 62 having varying thickness. In between the posts 62 are polymer layers 64 which may be, for example, formed of epoxy material. The composite material may, for example, be that described by R. E. Newnham et al. "Connectivity and Piezoelectric-Pyroelectric Composites", Materials Research Bulletin, Vol. 13 at 525–36 (1978) and R. E. Newnham et al., "Flexible Composite Transducers", Materials Research Bulletin, Vol. 13 at 599–607 (1978) which are incorporated herein by reference. The composite structure 60 is preferably plano-concave. An acoustic matching layer, not shown, may be disposed on the front portion 66 for increasing performance.

The composite material may be embedded in a polymer layer. Then, the composite material may be ground, machined, or formed to the desired size. In addition, the Individual transducer elements may be formed by sawing the composite structure, as is commonly done in the ultrasound industry. The gaps between each of the respective transducer elements may also be filled with polymer material to ensure electrical isolation between elements.

Although the front portion 66 is shown as a curved surface, the front portion 66 may include a stepped configuration, a series of linear segments, or any other configuration wherein the thickness of the structure 60 is greater at each of the side portions 70, 72 and decreases in thickness at the center. In addition, although the back portion 68 is shown as a flat surface, the back portion may be a generally planar surface, a concave or a convex surface. Electrodes 74 and 76, similar to the electrodes described earlier, may be placed on the front and back portions of the composite structure.

Figure 15:
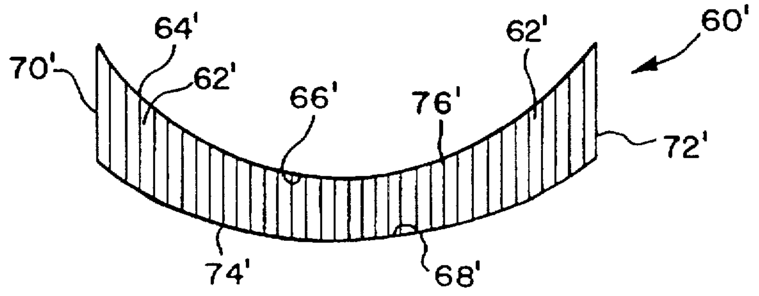
FIG. 15 is a cross-sectional view of the composite transducer element of FIG. 14 which is deformed.

The composite structure 60 of FIG. 14 may be deformed as shown in FIG. 15 resulting in both a concave portion 6' and a concave portion 68'. The deformed structure of FIG. 15 may result by mechanically deforming the structure of FIG. 14. In certain applications, the structure of FIG. 14 may be heated prior to deforming. If the filler material between the vertical posts 62 is made of silicone rather than an epoxy material, the structure of FIG. 14 may easily be deformed without the application of heat. If epoxy material is used, then the structure of FIG. 14 should be exposed to approximately 50° C. before deforming the structure. In addition, the composite structure may be deformed in the opposite direction, not shown, resulting in a concave portion 66' and a convex portion 68'. It should be noted that forming the transducer structure of FIG. 14 not only allows for a broadband transducer, but also generally provides focusing of the ultrasound beam in the region of interest. By deforming the structure as shown in FIG. 15, one is capable of "fine tuning" the focusing of the ultrasound beam.

In operation, the transducer array 10 may first be activated at a higher frequency along a given scan direction in order to focus the ultrasound beam at a point in the near field. The transducer may be gradually focused along a series of points along the scan line, decreasing the excitation frequency as the beam is gradually focused in the far field. Where the value of LMAX is greater than 140 percent the value of LMIN, the exiting beam width, which has a narrow aperture at high frequencies, may widen in aperture as the excitation frequency is decreased, as illustrated in FIG. 9. Eventually, at a low enough frequency, such as two Megahertz, the transducer 10 simulates a two-dimensional array by effectively generating a beam using the full aperture of the transducer elements 11. Further, the greater the curvature of front portion 12, the more the transducer 10 simulates a two-dimensional array. A matching layer 24 may also be disposed on the front portion 12 of element 11 in order to further increase bandwidth and sensitivity performance.

In addition, when performing contrast harmonic imaging, the transducer array elements 11 may first be excited at a dominant fundamental harmonic frequency, such as 3.5 Megahertz, to observe the heart or other tissue being observed. Then, the transducer array elements 11 may be set to the receive mode at a dominant second harmonic, such as 7.0 Megahertz, in order to make the contrast agent more clearly visible relative to the tissue. This will enable the observer to ascertain how well the tissue is operating. When observing the fundamental harmonic, filters (e.g., electrical filters) centered around the fundamental frequency may be used. When observing the second harmonic, filters centered around the second harmonic frequency may be used. Although the transducer array may be set to the receive mode at the second harmonic as described above, the transducer array may be capable of transmitting and receiving at the second harmonic frequency.

Figure 20:
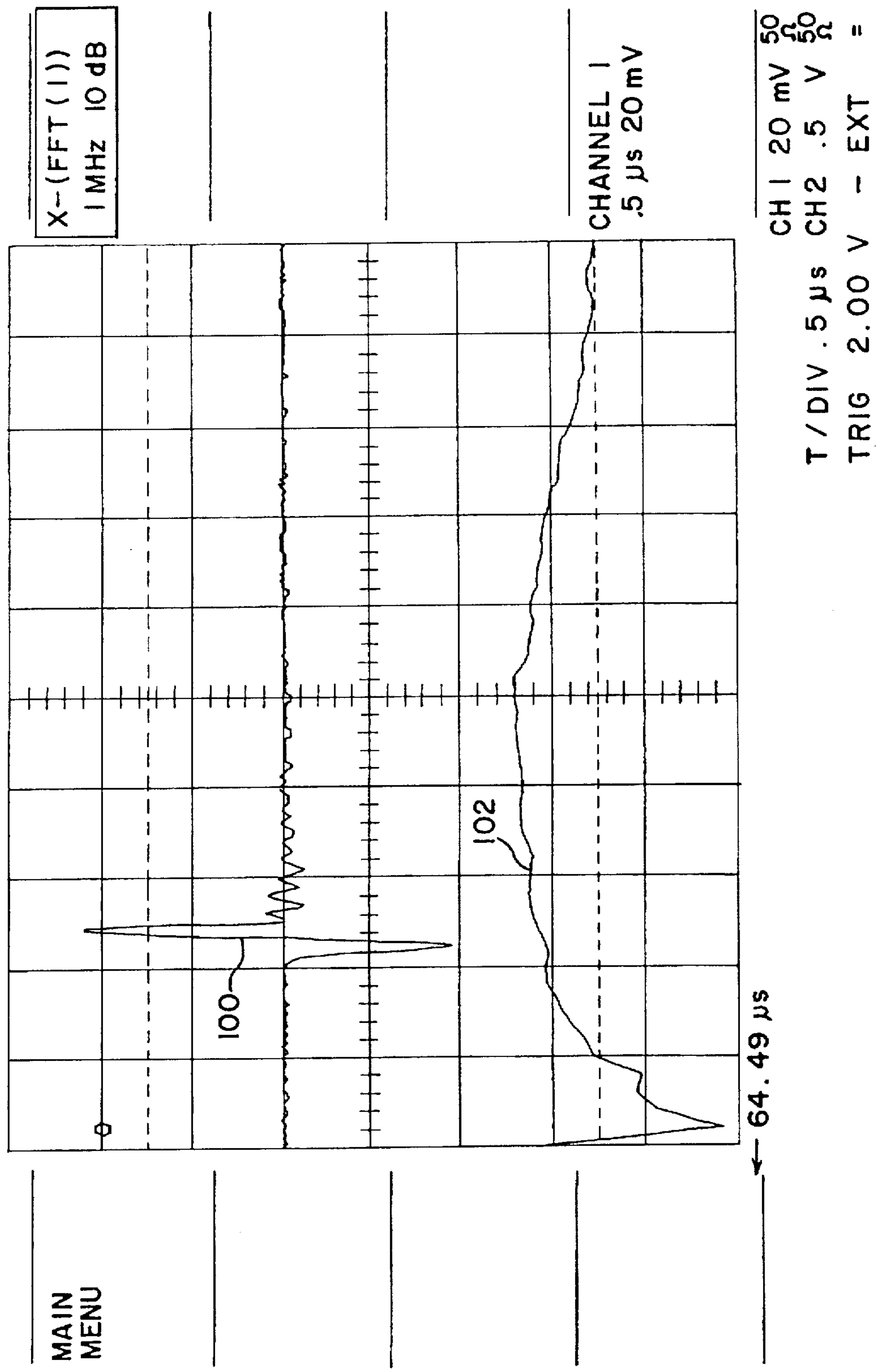
FIG. 20 shows an impulse response and the corresponding frequency spectrum for the transducer element of FIG. 6.

The application of pulses to obtain the desired excitation frequency is well known in the art. For illustrative purposes, referring now to FIG. 20, an impulse response 100 is shown having a width of approximately 0.25 usec. The impulse response 100 is the transducer response to an impulse excitation where LMIN is 0.109 mm, LMAX is 0.381 mm, and the radius of curvature of the front portion 12 is 103.54 mm. The impulse response 100 results in a frequency spectrum 102 ranging from approximately 1 MHz to 9 MHz.

It is desirable to excite the transducer element 11 with the use of an impulse excitation when viewing the far field or in applications where one is not limited to selecting a given aperture of the transducer element 11 for producing an ultrasound beam. Exciting the whole aperture of the transducer element 11 also helps produce a finer resolution along the range axis.

To select the aperture of the central portion 19 of transducer element when viewing the near field, a series of pulses, approximately 2 to 5 pulses, may be used to excite the transducer element 11. The pulses have a frequency correlating to the central portion 19 of the element 11. Typically, the frequency of the pulses is approximately 7 MHz and the width of the pulses is approximately 0.14 usec.

To simulate a two-dimensional array at lower frequencies, as discussed earlier, a series of pulses, approximately 2 to 5 pulses, may be applied to excite the transducer element 11. The pulses have a frequency which matches the resonance frequency correlating to the thickest or side portions 16, 18 of the transducer element. Typically, the frequency of the pulses is approximately 2.5 MHz and the width of the pulses is approximately 0.40 usec. This helps produce a clearer image when viewing the far field.

The elements 11 for the single crystal design shown in FIGS. 3, 5, and 18 each measure 15 mm in the elevation direction and 0.0836mm in the azimuthal direction. The element spacing S is 0.109 mm and the length of the kerf is 25.4um. The thickness LMIN is 0.109 mm and the thickness LMAX is 0.381 mm. The radius of curvature of the front portion 12 is 103.54 mm.

The backing block is formed of a filled epoxy comprising Dow Corning's part number DER 332 treated with Dow Corning's curing agent DEH 24 and has an Aluminum Oxide filler. The backing block for a transducer array comprising 128 elements has dimensions of 20 mm in the azimuthal direction, 16 mm in the elevation direction, and 20 mm in the range direction.

The shape and dimension of the matching layer 24 is approximated by the equation LML=(½) (LE) (CML/CE) where, for a given point on the transducer surface, LML is the thickness of the matching layer, LE is the thickness of the transducer element, CML is the speed of sound of the matching layer, and CE is the speed of sound of the element. The transducers may be used with commercially available units such as Acuson Corporation's 128 XP System having acoustic response technology (ART) capability.

For the two crystal design of FIG. 12, the first and second piezoelectric portions 42 and 44 have a minimum thickness of 0.127 mm and a maximum thickness of 0.2794 mm, as measured in the range direction. The radius of curvature for the surfaces 46 and 48 of piezoelectric portions 42 and 44 are 184.62 mm. The element spacing S is 0.254 mm and the length of the kerf is 25.4 um.

For the two crystal design of FIG. 13, piezoelectric portions 56 and 57 have a minimum thickness of 0.127 mm and maximum thickness of 0.2794 mm. The radius of curvature of the front portion 63 of the first piezoelectric portion 56 and the back portion 65 of the second piezoelectric portion is 184.62 mm. The radius of curvature of the front portion 67 of piezoelectric portion 57 is 92.426 mm.

Finally, the composite structure design shown in FIG. 14 preferably has dimensions similar to that for FIGS. 4 or 5, forming an array of 128 transducer elements. The structure of FIG. 11 further possesses a generally planar back portion 68 which is especially desirable when focusing in the far field. The structure of FIG. 15 may be formed by deforming the ends of the structure of FIG. 14 in the range direction.

Where focusing in the near field at approximately 2 cm into the body being examined, the side portions of the structure of FIG. 14 should be deformed by approximately 0.25 mm relative to the center portion.

Each of the backing block, the flex circuit, the piezoelectric layer, the matching layer, and the coupling element may be glued together by use of any epoxy material. A Hysol® base material number 2039 having a Hysol® curing agent number HD3561, which is manufactured by Dexter Corp., Hysol Division of Industry, California, may be used for gluing the various materials together. Typically, the thickness of epoxy material is approximately 2 um.

The flex circuit thickness for forming the first electrode is approximately 25 um for a flex circuit manufactured by Sheldahl for providing the appropriate electrical excitation. The thickness of the second electrode is typically 2000–3000 Angstroms and may be disposed on the transducer structure by use of sputtering techniques.

It should be noted that the transducer array constructed in accordance with the present invention may be capable of operating at the third harmonic, such as 10.5 Megahertz in this example. This may further provide additional information to the observer. Moreover, the addition of the matching layer 24 will enable the transducer array to operate at an even broader range of frequencies. Consequently, this may further enable a transducer of the present invention to operate at both a certain dominant fundamental and second harmonic frequency.

It is to be understood that the forms of the invention described herewith are to be taken as preferred examples and that various changes in the shape, size and arrangement of parts may be resorted to, without departing from the spirit of the invention or scope of the claims.

We claim:

1. An ultrasonic transducer array for testing a body, comprising:
   - a plurality of transducer elements aligned along an array axis; and
   - a backing support that supports the plurality of transducer elements;
   - wherein each of the plurality of transducer elements in the array includes
     - a piezoelectric layer having a front surface overlaid by a front electrode and a rear surface overlaid by a rear electrode, the front surface being concave along an axis perpendicular to the array axis and the piezoelectric layer having a non-uniform thickness wherein the thickness is smallest near the center of the layer and largest at each end of the layer wherein the thickness of the piezoelectric layer continuously increases from the smallest to the largest thickness, and
     - a first acoustic matching layer having a front surface that is concave along an axis perpendicular to the array axis, a rear surface, and a uniform thickness, the rear surface of the acoustic matching layer being mounted to the concave front surface of the piezoelectric layer;
   - wherein each of the plurality of transducer elements in the array has its piezoelectric layer and at least a portion of its first acoustic matching layer spaced from the adjacent transducer elements in the array; and
   - wherein the concave shapes of the front surfaces of the piezoelectric and acoustic matching layers of each transducer element are selected to mechanically focus the transducer elements in a plane perpendicular to the array axis.

2. The ultrasonic transducer array of claim 1, wherein each of the plurality of transducer elements further includes a second acoustic matching layer having a concave front surface, a rear surface and uniform thickness, mounted to the concave front surface of the first acoustic matching layer.

3. The ultrasonic transducer array of claim 1, wherein a flexible printed circuit signal conductor is attached to the rear electrode of each of the plurality of transducer elements and a flexible ground conductor is attached to the front electrode of each of the plurality of transducer elements.

4. The ultrasonic transducer array of claim 3, wherein each of the plurality of transducer elements is divided into subelements, with the subelements electrically connected in parallel.

5. The ultrasonic transducer array of claim 1, further comprising a coupling element formed of an unfilled polyurethane wherein said coupling element forms an outer face layer for the plurality of transducer elements.

6. The ultrasonic transducer array of claim 1, wherein the spaces between adjacent transducer elements is filled with a polymer material to ensure electrical isolation between elements.

7. The ultrasonic transducer array of claim 1, wherein, for each transducer element, the front surface of the piezoelectric layer is interrupted by a series of slots arranged in the direction of the array axis, each transducer element further comprising means for providing an electrically conductive path across the series of slots.

8. The ultrasonic transducer array of claim 7, wherein the means for providing an electrically conductive path includes an electrically conductive layer between the piezoelectric layer and the acoustic matching layer of each transducer element.

9. The ultrasonic transducer array of claim 7, wherein the means for providing an electrically conductive path is the acoustic matching layer, wherein the acoustic matching layer is an electrically conductive material.

10. The ultrasonic transducer array of claim 7, wherein, a flexible printed circuit signal conductor is attached to the rear electrode of each of the plurality of transducer elements and a flexible ground conductor is attached to the front electrode of each of the plurality of transducer elements.

11. The ultrasonic transducer array of claim 10, wherein each of the plurality of transducer elements is divided into subelements, with the subelements electrically connected in parallel.

12. The ultrasonic transducer array of claim 7, further comprising a coupling element formed of an unfilled polyurethane wherein said coupling element forms an outer face layer for the plurality of transducer elements.

13. The ultrasonic transducer array of claim 7, wherein the spaces between adjacent transducer elements is filled with a polymer material to ensure electrical isolation between elements.

14. The ultrasonic transducer array of claim 7, wherein the array axis has a convex shape facing the body being tested.

15. The ultrasonic transducer array of claim 7, wherein the series of slots for each transducer element are uniformly spaced.

16. The ultrasonic transducer array of claim 7, wherein the first acoustic matching layer of each of the plurality of transducer elements in the array is completely spaced apart from the first acoustic matching layer of the adjacent transducer elements in the array.

17. The ultrasonic transducer array of claim 7, wherein the array axis is linear and the plurality of transducer elements are uniformly spaced along the array axis.

18. The ultrasonic transducer array of claim 7, wherein the array axis is curvilinear and the plurality of transducer elements are uniformly spaced along the array axis.

19. The ultrasonic transducer array of claim 7, wherein the array axis includes a linear and curvilinear sections and the plurality of transducer elements are uniformly spaced along the array axis.

20. The ultrasonic transducer array of claim 7, wherein for each transducer element, the piezoelectric layer is a PZT-based material.

21. The ultrasonic transducer array of claim 7, wherein for each transducer element, the piezoelectric layer is a PVDF-based material.

22. The ultrasonic transducer array of claim 1, wherein the array axis has a convex shape facing the body being tested.

23. The ultrasonic transducer array of claim 7, wherein each of the plurality of transducer elements further includes a second acoustic matching layer having a concave front surface, a rear surface and uniform thickness, mounted to the concave front surface of the first acoustic matching layer.

24. The ultrasonic transducer array of claim 8, wherein the front and rear electrodes each include a layer of copper.

25. The ultrasonic transducer array of claim 1, wherein the array the array axis is linear and the plurality of transducer elements are uniformly spaced along the array axis.

26. The ultrasonic transducer array of claim 1, wherein the array axis is curvilinear and the plurality of transducer elements are uniformly spaced along the array axis.

27. The ultrasonic transducer array of claim 1, wherein the array axis includes linear and is curvilinear sections and the plurality of transducer elements are uniformly spaced along the array axis.

28. The ultrasonic transducer array of claim 1, wherein for each transducer element, the piezoelectric layer is a PZT-based material.

29. The ultrasonic transducer array of claim 1, wherein for each transducer element, the piezoelectric layer is a PVDP-based material.

* * * * *

UNITED STATES PATENT AND TRADEMARK OFFICE

CERTIFICATE OF CORRECTION

PATENT NO. : 5,743,855
DATED : April 28, 1998
INVENTOR(S) : Amin M. Hanafy et al.

It is certified that error appears in the above-indentified patent and that said Letters Patent is hereby corrected as shown below:

On the Title Page , item [56]

In column 2, line 3, under "OTHER PUBLICATIONS", change "Stimulated" to --Simulated--.

In column 2, line 9, under "OTHER PUBLICATIONS", change "Pizoelectric" to --Piezoelectric--.

On page 2, column 2, line 6, under "U.S. PATENT DOCUMENTS", change "Maerfield" to --Maerfeld--.

UNITED STATES PATENT AND TRADEMARK OFFICE

CERTIFICATE OF CORRECTION

PATENT NO. : 5,743,855

DATED : April 28, 1998

INVENTOR(S) : Amin M. Hanafy et al.

It is certified that error appears in the above-indentified patent and that said Letters Patent is hereby corrected as shown below:

In the Claims (cont'd)

In claim 25, line 2, delete "the array" (second occurrence).

In claim 27, line 2, delete "is".

Signed and Sealed this

Second Day of May, 2000

Attest:

Q. TODD DICKINSON

Attesting Officer

*Director of Patents and Trademarks*

UNITED STATES PATENT AND TRADEMARK OFFICE
CERTIFICATE OF CORRECTION

PATENT NO. : 5,743,855
DATED : April 28, 1998
INVENTOR(S) : Amin M. Hanafy, et al.

It is certified that error appears in the above-identified patent and that said Letters Patent is hereby corrected as shown below:

On the Title Page

Column 1,
Line 7, under "U.S. PATENT DOCUMENTS", change "4,447,715" to - 4,442,715--.
Line 7, under "U.S. PATENT DOCUMENTS", change "5/1984" to --4/1984--.

Signed and Sealed this

Seventeenth Day of July, 2001

*Attest:*

Nicholas P. Godici

NICHOLAS P. GODICI

*Attesting Officer* *Acting Director of the United States Patent and Trademark Office*